United States Patent
Roffman et al.

(10) Patent No.: US 6,695,880 B1
(45) Date of Patent: Feb. 24, 2004

(54) INTRAOCULAR LENSES AND METHODS FOR THEIR MANUFACTURE

(75) Inventors: Jeffrey H. Roffman, Jacksonville, FL (US); Frank F. Molock, Orange Park, FL (US); Gregory A. Hill, Atlantic Beach, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 09/696,349

(22) Filed: Oct. 24, 2000

(51) Int. Cl.[7] ................................. A61F 2/16
(52) U.S. Cl. ..................... 623/6.28; 623/6.29
(58) Field of Search ............... 623/6.11, 6.19, 623/6.2, 6.21, 6.28, 6.23, 6.29, 6.24, 6.27, 6.37

(56) References Cited

U.S. PATENT DOCUMENTS

| | | | |
|---|---|---|---|
| 4,253,199 A | | 3/1981 | Banko |
| 4,409,691 A | | 10/1983 | Levy |
| 4,731,078 A | * | 3/1988 | Stoy et al. ............... 623/6.28 |
| 4,731,079 A | * | 3/1988 | Stoy ........................ 623/6.28 |
| 4,790,847 A | | 12/1988 | Woods |
| 4,842,601 A | | 6/1989 | Smith |
| 4,892,543 A | | 1/1990 | Turley |
| 4,898,461 A | * | 2/1990 | Portney ................... 351/169 |
| 4,932,966 A | | 6/1990 | Christie et al. |
| 5,096,285 A | * | 3/1992 | Silberman ............... 351/161 |
| 5,152,787 A | * | 10/1992 | Hamblen ................. 623/6.19 |
| 5,158,572 A | | 10/1992 | Nielsen |
| 5,166,712 A | * | 11/1992 | Portney ................... 351/161 |
| 5,275,623 A | | 1/1994 | Sarfarazi |
| 5,489,302 A | | 2/1996 | Skottun |
| 5,507,806 A | | 4/1996 | Blake |
| 5,521,656 A | * | 5/1996 | Portney ................... 351/177 |
| 5,570,142 A | * | 10/1996 | Lieberman ............... 351/160 |
| 5,607,472 A | | 3/1997 | Thompson |
| 5,715,031 A | * | 2/1998 | Roffman et al. ......... 351/161 |
| 5,777,719 A | | 7/1998 | Williams et al. |
| 5,843,188 A | | 12/1998 | McDonald |
| 5,877,839 A | | 3/1999 | Portney |
| 6,013,101 A | | 1/2000 | Israel |
| 6,027,672 A | | 2/2000 | Weitzel et al. |
| 6,086,204 A | | 7/2000 | Magnante |
| 6,089,711 A | | 7/2000 | Blankenbecler et al. |
| 6,095,651 A | | 8/2000 | Williams et al. |
| 6,186,625 B1 | * | 2/2001 | Portney ................... 623/6.28 |
| 6,236,493 B1 | * | 5/2001 | Schmidt et al. ......... 359/296 |
| 6,409,340 B1 | * | 6/2002 | Portney ................... 351/161 |
| 6,413,276 B1 | * | 7/2002 | Werblin .................. 623/6.32 |

FOREIGN PATENT DOCUMENTS

| | | |
|---|---|---|
| FR | 2655842 A | 6/1991 |
| WO | WO 86/03961 | 7/1986 |
| WO | WO 92/10980 | 7/1992 |
| WO | WO 99/27334 | 6/1999 |

OTHER PUBLICATIONS

PCT International Search Report, dated Jul. 8, 2002 for PCT Appln. No. PCT/US01/29733 which relates to U.S. patent appln. No. 09/696,349, filed Oct. 24, 2000.

* cited by examiner

*Primary Examiner*—David H. Willse
*Assistant Examiner*—Suzette J. Jackson
(74) *Attorney, Agent, or Firm*—Lois Gianneschi

(57) ABSTRACT

The present invention provides intra ocular lenses that have a refractive index gradient. Additionally, the lenses of the invention may be customized to correct the ocular wave front aberrations of a particular individual.

7 Claims, 1 Drawing Sheet

INTRAOCULAR LENSES AND METHODS FOR THEIR MANUFACTURE

FIELD OF THE INVENTION

The present invention relates to intra ocular lenses. In particular, the invention provides intra ocular lenses that have a refractive index gradient. Additionally, the lenses of the invention may be customized to a particular individual.

BACKGROUND OF THE INVENTION

The use of intra ocular lenses to replace a patient's natural lens is well known. Generally, the intra ocular lenses are formed by lathe cutting, molding, or the like. The lenses may be fixed within the eye, such as by haptics, which typically are attached in a secondary step. The lenses may be accommodating lenses that move along the optical axis of the eye to provide correction for distance and near vision. Known intra ocular lenses are made of rigid materials such as polymethyl methacrylate and the like or flexible materials such as silicone, hydrogels, fluorocarbons, hydroxyethyl methacrylate, and the like.

Conventional intra ocular lenses are disadvantageous in that the lenses are of a single refractive index, but are used to replace the natural lens which has a gradient refractive index. Additionally, the known intra ocular lenses provide no correction for high order ocular aberrations nor are they customized to a particular individual. Therefore, a need exists for a intra ocular lenses and methods for their production that overcome these disadvantages.

DESCRIPTION OF THE INVENTION AND ITS PREFERRED EMBODIMENTS

Figure 1:
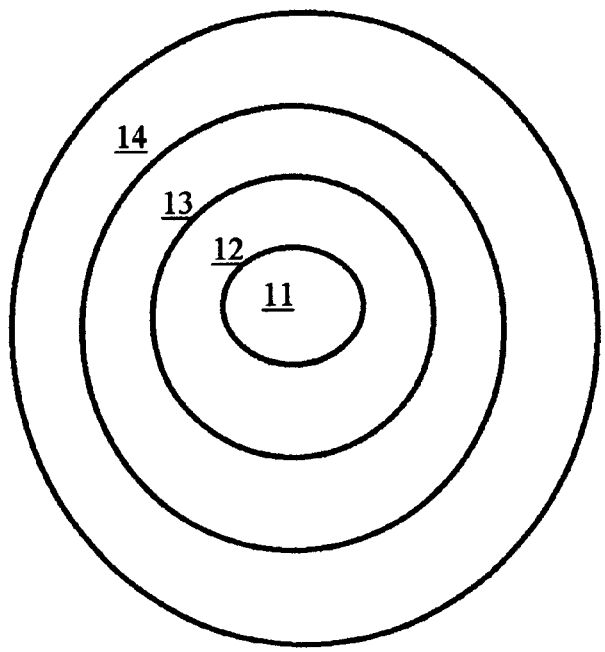
FIG. 1 is a magnified, cross-sectional plan view of the lens of the invention.

The present invention provides intra ocular lenses that incorporate one or both of a refractive index gradient and correction for ocular wave front aberrations. The refractive index gradient provides a lens that is more similar to the natural crystalline lens than known intra ocular lenses. Additionally, the lenses of the invention provide for a level of vision correction not previously available in intra ocular lenses.

The invention provides an intra ocular lens comprising, consisting essentially of, and consisting of a refractive index gradient. The intra ocular lenses of the invention may be of the type that are fixed as to centration within the eye, but move forwardly and backwardly due to ciliary muscle action. Alternatively, the lens may be an accommodating lens meaning that the lens is attached to the capsule, but is capable of changing radius and shape.

It is one discovery of the invention that by incorporating a refractive index gradient into an intra ocular lens, the performance of the lens will be improved. In the lens of the invention, a refractive index gradient is provided, which gradient may be formed by use of at least two layers of materials of differing refractive indices. Generally, about 3 to about 12 layers may be used; preferably, about 4 to about 6 layers are used. In the lenses of the invention, the refractive index, from the center, or innermost layer, of the lens to its outer-most layer, may increase or decrease. Preferably, the refractive index decreases as one moves from the innermost to the outermost layers and ranges from about 1.52 to about 1.38, more preferably about 1.50 to about 1.46, most preferably about 1.44 to about 1.40. For those lenses made from rigid materials, preferably the refractive index ranges from about 1.52 to about 1.48 from the center to the outer-most layer. For flexible materials, the range is about 1.50 to about 1.46. The change in index between the layers may be equal or unequal. Similarly, the thickness of the layers may be unequal or, preferably, equal.

The lenses of the invention may be made of any material suitable for forming intra ocular lenses. For example, the lenses may be made from a rigid material including, without limitation, polymethyl methacrylate, polystyrene, polycarbonate, or the like, and combinations thereof. Additionally, flexible materials may be used including, without limitation, hydrogels, silicone materials, acrylic materials, fluorocarbon materials and the like, or combinations thereof For purposes of forming the inner most layer of the lens, a high refractive index monomer may be selected and polymerized or a first monomer with a first refractive index may be polymerized with a second monomer having a second refractive index in order to provide the refractive index desired. Preferably, the monomers used to form the lenses of the invention are free-radical reactive monomers.

In those lenses produced using rigid materials, the refractive index of the material may be varied by the addition of an aromatic methacrylate, halomethacrylate, or an aromatic halomethacrylate, or combinations thereof in an amount effective to increase or decrease the material to the desired level. Suitable aromatic methacrylates include, without limitation, phenyl methacrylate, naphthyl methacrylate, phenylethyl methacrylate, methoxyphenyl methacrylate, o-crsyl methacrylate, and the like, and combinations thereof. Halomethacrylates useful in the invention include, without limitation, polyfluoroalkyl methacrylates, 2-chloroethyl methacrylates, 2-bromomethacrylate, chlorocyclohexyl methacrylate, bromocyclohexylmethacrylate, and the like, or combinations thereof. Suitable aromatic halomethacrylates include, without limitation, chlorobenzyl methacrylate, bromobenzyl methacrylate, and the like, or combinations thereof Similarly, these materials may be used to alter the refractive index of a flexible material such as a hydrogel or acrylic material to the desired level. In addition, chloro- or bromostyrenes may be used. For lenses made from silicone materials, the desired refractive index may be obtained by use of poly(dimethyl-co-phenylmethyl) siloxane to the material.

The materials used to form the lens may be polymerized by any known means, such as thermal, photochemical, or radiation cure using any suitable initiator including, without limitation, a thermal initiator, a UV initiator, a visible light initiator, and the like, or a combination thereof To form the lenses of the invention, the inner-most layer may be formed by casting a rod of material of the desired refractive index and placing the rod in the center of a mold. The next lower refractive index material is dispensed into the mold and polymerized. The process may be repeated to add the desired number of layers of varying refractive index to form an intra ocular lens blank. The rod then is removed from the mold, cut, and machined to form a gradient refractive index lens.

Alternatively, laminar flow mixed dosing may be used in which at least two monomers of different refractive index are dispensed with inline mixing into a mold, dispensing the low index material prior to the high index material. The flow rate is adjusted so that no mixing occurs in the mold. The dispensed material then is cured to produce a linear gradient index lens.

The conditions under which the materials are cured will depend on the method selected to produce the lens and the materials being used to form the lens. It is within the skill of one of ordinary skill in the art to determine the precise cure conditions.

In forming the lens, the flexibility of the material becomes more critical as one moves from the inner-most layer to the outermost layer, the outermost layers being the more flexible. This may be controlled by a number of factors including, without limitation, the glass transition temperature, modulus, and water content of the material. In formation of the layers making up the lens, the compatibility of one layer with another to be added to it may be increased by treatment, such as by plasma treatment, prior to addition of the next layer.

The lenses of the invention may be anchored within the lens capsule by any known means such as the use of haptics. Additionally, a photoreactive tissue cement may be used including, without limitation, fibrin, cyanoacrylate, photocurable gelatin, and the like, or combinations thereof. Means for anchoring the lenses within the eye for both fixed and accommodating lenses are well known. The lenses of the invention may be implanted in any region into which intra ocular lenses are typically implanted such as the anterior or posterior chamber, or any of a variety of positions in or on the cornea.

In FIG. 1 is depicted lens 10 of the invention. Lens 10 has innermost layer 11 having a refractive index of 1.50. Layer 12 overlays layer 11 and is of a refractive index of 1.49. Similarly, layers 13 and 14 overlay layers 12 and 13, respectively, each having a refractive index of 1.48 and 1.47, respectively.

In another embodiment, the invention provides an intra ocular lens for an individual comprising, consisting essentially of, and consisting of an anterior and a posterior surface, wherein one or both of the surfaces is suitable to substantially correct one or more wave front aberrations of the individual. In yet another embodiment, the invention provides an intra ocular lens for an individual comprising, consisting essentially of, and consisting of a refractive index gradient, an anterior surface, and a posterior surface, wherein one or both of the surfaces is suitable to substantially correct one or more ocular wave front aberrations of the individual.

Ocular waterfront aberrations, generally, are wave front aberrations of the eye that are departures from a spherical waterfront at any position on the waterfront. The classic description of these aberrations are spherical aberration, astigmatism, coma, and distortion.

Alternatively, the aberrations may be mathematically described, for example using Zernike polynomials. Apparatuses for performing the aberration measurements include, without limitation, aberroscopes, devices that measure ocular Modulation Transfer Function by point spread or line spread, or any similar devices that measure, estimate, interpolate, or calculate the ocular optical waterfront. A suitable aberroscope for carrying out the measurements is available from Waterfront Sciences, Inc, Albuquerque, N. Mex. Preferably, the intra ocular lenses of the invention correct high order ocular waterfront aberrations.

The lenses of the invention may be designed to provide multifocal correction. For example, in the case of the designing of an accommodating intra ocular lens, the waterfront measurement of the eye may be carried out by providing the lens wearer visual targets at at least two different distances, a first and a second distance. For example, one target may be provided in the lens wearer's distance vision zone, the target being about 15 feet or more from the eye. A second target may be provided in the near vision zone, the target being about 30 to about 50 cm from the eye. Preferably, a target also is provided in the lens wearer's intermediate vision zone, the target being about 50 to about 80 cm from the wearer's eye. It is known in the art how to utilize available devices available for aberration measurement at far, near and intermediate distances.

After the aberration measurements are obtained, the measurements are mathematically converted to a height difference thus providing an elevation map above and below a designated mean sphere value, known as the optical path difference. Correction for the aberrations will be provided by introduction of an optical path difference, or aberration inverse filter, that offsets the distortions due to the ocular aberrations.

The converted differences are used to provide the desired lens. The data may be transformed onto a grid pattern of a rectilinear, polar concentric, or spiral format to correspond to the mechanism by which the surface of the lens, or a mold used to form the lens, may be tooled using a computer numeric controlled ("CNC") lathe. The required changes in the lens' surface elevation or slope to achieve correction of the aberrations may be incorporated onto the lens' front surface, back surface, or a combination thereof.

In the cases in which the lenses of the invention are multifocal, one or both of the front, or convex, surface and back, or concave, surface of the lens may contain an optic zone that corrects the lens wearer's ocular waterfront aberrations for distance, near, and optionally intermediate vision. In an alternative embodiment, aberration correction may be divided between the front and back surfaces.

In addition to waterfront aberration compensating surfaces, one or more surfaces of the intra ocular lens may be of a geometry that substantially corresponds with that of the lens wearer's cornea. The corneal topographic data for the lens wearer may be acquired using conventional topographers.

What is claimed is:

1. An intraocular lens, comprising a refractive index gradient comprising at least three layers of materials of differing refractive indices, wherein the lens provides multifocal correction.

2. The intraocular lens of claim 1, comprising about 3 to about 12 layers of materials of differing refractive indices.

3. The intraocular lens of claim 1, wherein, from the innermost layer of the lens to its outermost layer, the refractive indices of the layers range from about 1.52 to about 1.38.

4. An intraocular lens for an individual, comprising an anterior surface, a posterior surface and a refractive index gradient comprising at least three layers of materials of differing refractive indices, wherein one or both of the surfaces is suitable to substantially correct one or more high order ocular waterfront aberrations of the individual.

5. The intraocular lens of claim 4, comprising about 3 to about 12 layers of materials of differing refractive indices.

6. The intraocular lens of claim 4, wherein, from the innermost layer of the lens to its outermost layer, the refractive indices of the layers range from about 1.52 to about 1.38.

7. The intraocular lens of claim 4, further comprising one or more surfaces of a geometry that substantially corresponds to the individual's corneal topography.

* * * * *